(12) United States Patent
Horvath

(10) Patent No.: US 9,050,190 B2
(45) Date of Patent: Jun. 9, 2015

(54) DEVICE COMPRISING A SWELLING AGENT AND SHEATHING FOR ARTIFICIAL CALLUS DISTRACTION

(75) Inventor: Domonkos Horvath, Jestetten (DE)

(73) Assignee: CELGEN3D AG, Zug (CH)

( * ) Notice: Subject to any disclaimer, the term of this patent is extended or adjusted under 35 U.S.C. 154(b) by 595 days.

(21) Appl. No.: 12/922,534

(22) PCT Filed: Mar. 14, 2009

(86) PCT No.: PCT/EP2009/001875
§ 371 (c)(1),
(2), (4) Date: Sep. 14, 2010

(87) PCT Pub. No.: WO2009/115251
PCT Pub. Date: Sep. 24, 2009

(65) Prior Publication Data
US 2011/0009978 A1   Jan. 13, 2011

(30) Foreign Application Priority Data
Mar. 15, 2008   (DE) .......................... 10 2008 014 560

(51) Int. Cl.
*A61F 2/28* (2006.01)
*A61B 17/66* (2006.01)
*A61L 27/34* (2006.01)
*A61L 27/50* (2006.01)
*A61B 17/00* (2006.01)

(52) U.S. Cl.
CPC ................. *A61F 2/28* (2013.01); *A61B 17/666* (2013.01); *A61B 2017/00898* (2013.01); *A61L 27/34* (2013.01); *A61L 27/50* (2013.01); *A61L 2430/02* (2013.01)

(58) Field of Classification Search
CPC .......................... A61F 2/28; A61B 2017/00898
USPC ............................................. 623/17.17, 23.52
See application file for complete search history.

(56) References Cited

U.S. PATENT DOCUMENTS

| 6,511,510 | B1 | 1/2003 | de Bruijn |
| 7,749,267 | B2 | 7/2010 | Karmon |
| 2004/0115240 | A1 * | 6/2004 | Narhi et al. ................... 424/426 |

(Continued)

FOREIGN PATENT DOCUMENTS

| DE | 102004043325 A1 | 4/2005 |
| WO | WO 01/91663 A1 | 12/2001 |

(Continued)

OTHER PUBLICATIONS

International Search Report for PCT/EP2009/001875, ISA/EP, Rijswijk, NL, mailed Aug. 6, 2009.
International Preliminary Report on Patentability with annex and translation of annex, IPEA/EP, Munchen, Feb. 7, 2010.

(Continued)

*Primary Examiner* — Bruce E Snow
*Assistant Examiner* — Melissa Hoban
(74) *Attorney, Agent, or Firm* — Stephen T. Olson; Harness, Dickey & Pierce, P.L.C.

(57) ABSTRACT

A device for regenerating a bone includes a sheathing and a swelling agent. At least a portion of the sheathing has the shape of a bellows, and/or the exterior of the sheathing bears at least one lamella. The swelling agent is enclosed by the sheathing. The sheathing is biocompatible, expandable, contractible, and/or deformable in a predefined and controlled manner as a function of a force effect induced by a change in volume of the swelling agent.

26 Claims, 7 Drawing Sheets

(56) References Cited

U.S. PATENT DOCUMENTS

Figure 1:
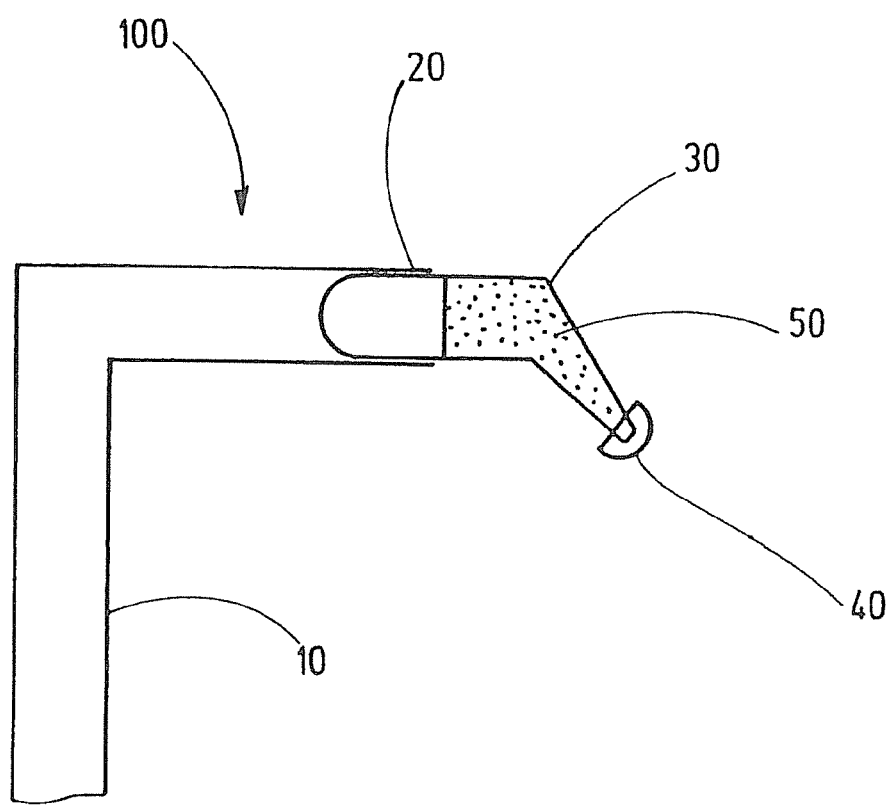

| | | |
|---|---|---|
| 2005/0209595 A1 | 9/2005 | Karmon |
| 2007/0005140 A1 | 1/2007 | Kim |
| 2007/0059827 A1* | 3/2007 | Horvath .................. 435/375 |
| 2007/0156251 A1 | 7/2007 | Karmon |
| 2008/0103518 A1 | 5/2008 | Karmon |
| 2009/0101157 A1 | 4/2009 | Karmon |
| 2010/0049330 A1 | 2/2010 | Horvath |

FOREIGN PATENT DOCUMENTS

| | | |
|---|---|---|
| WO | WO 02/074356 A1 | 9/2002 |
| WO | WO 2004/043303 A2 | 5/2004 |
| WO | WO 2008/043484 A2 | 4/2008 |

OTHER PUBLICATIONS

English Translation of International Preliminary Report on Patentability for Application No. PCT/EP2009/001875.

* cited by examiner

Fig. 5
A
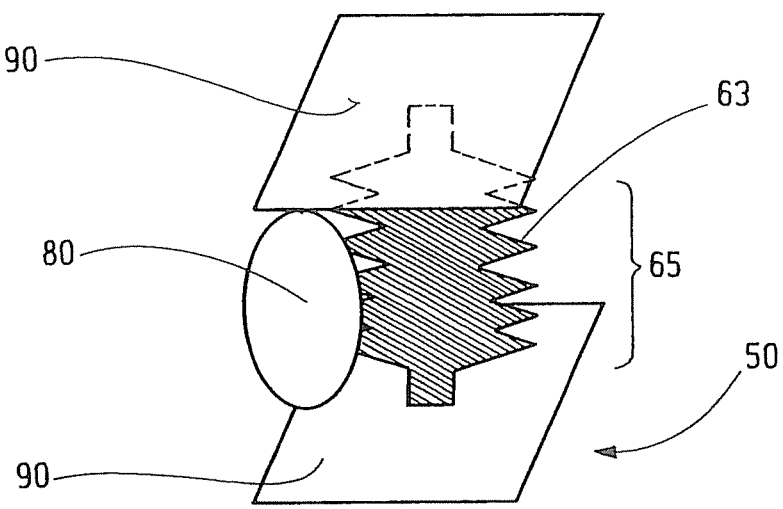
B
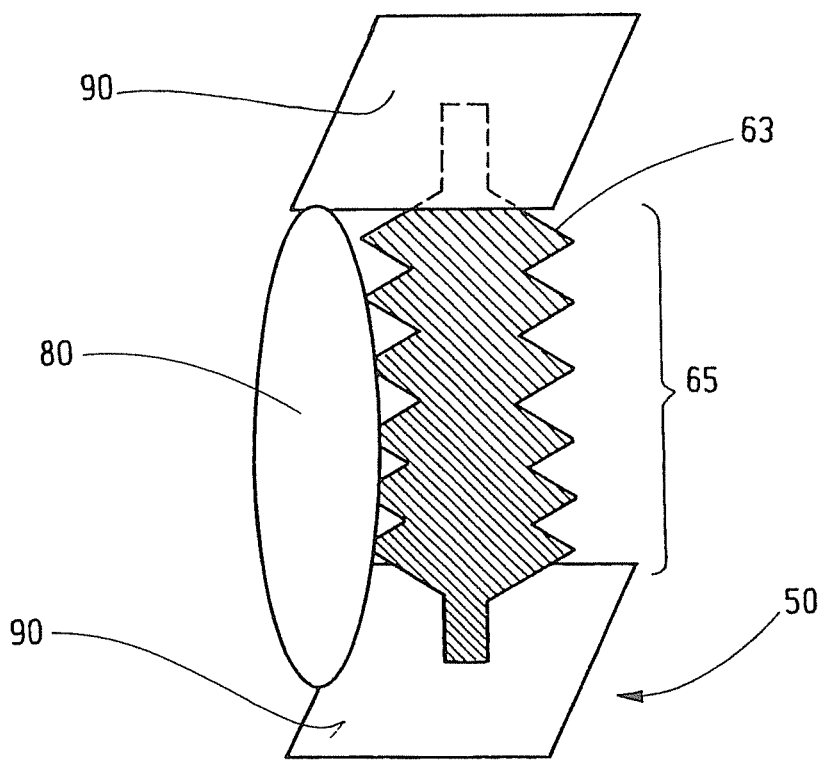

DEVICE COMPRISING A SWELLING AGENT AND SHEATHING FOR ARTIFICIAL CALLUS DISTRACTION

CROSS-REFERENCE TO RELATED APPLICATIONS

This application is a 371 U.S. National Stage of International Application No. PCT/EP2009/001875, filed Mar. 14, 2009. This application claims the benefit of German Patent Application No. DE 10 2008 014 560.2, filed Mar. 15, 2008, the disclosures of which applications are entirely incorporated by reference herein.

FIELD

The present invention relates to a device for regenerating a bone, in particular by means of three-dimensional distraction, a method for three-dimensional callus distraction, and use of the device.

BACKGROUND

At the present time, bone losses are generally filled using bone replacement materials, or autogenic or allogenic bone.

Examples of bone replacement materials include inorganic materials such as calcium phosphate, hydroxyapatite, or bioglass, which are replaced by bone after a long absorption period. However, this procedure may be used only for minor defects; otherwise, there is the risk of infection due to insufficient vascularization. The absorption of inorganic materials is inadequate. Such bone materials, i.e., bone replacement materials, do not emit biomechanical pulses and therefore do not initiate active regeneration. Also used are synthetically manufactured organic materials, such as polyesters, polyamino acids, polyanhydrides, polyorthoesters, polyphosphazenes, polylactides, or polyglycolides, or allogenic organic materials, for example of bovine origin. Material combinations of the various types of materials are also used as bone replacement composites. However, bone substance losses may also be compensated for using microvascular connected autogenic or allogenenically vascularized transplants. However, use of an allogenic bone replacement may trigger undesired immune reactions and transmit infection.

From a biological standpoint, the best replacement material for bone is an autologous spongiosa transplant. However, such transplants have limited availability and exhibit a high absorption rate after transplantation.

The materials and techniques used in the prior art frequently provide unsatisfactory bone quality, resulting, for example, in insecure anchoring of implant beds. In addition, frequently the bone replacement is insufficiently vascularized, thereby increasing the risk of infection. Furthermore, methods of the prior art often use growth factors which greatly increase the costs for the methods.

Instead of using a bone replacement, missing bone substance may sometimes be filled by bone regeneration. Segmented interruptions in the osseous continuity of long tubular bones may be treated in this manner by distraction osteogenesis.

Callus distraction has been known for over a hundred years. The most important biological stimulus for bone formation is mechanical stress. This releases piezoelectric forces which activate the osteoblasts and osteoclasts. Distraction osteogenesis induces new bone formation by triggering biological growth stimuli by means of slow separation of bone segments. This method achieves direct formation of woven bone by distraction. The defined tensile stress is essential for bone formation. When such a defined tensile stress is applied to bone fragments, the mesenchymal tissue exhibits an osteogenetic potential in the gap and at the contiguous fragment ends. When sufficient vascular potency is present, progressive distraction results in metaplasia of the organized hematoma, also referred to as blood coagulum, in a zone of longitudinally arranged fibrous tissue, which under optimal external and internal conditions may be directly converted to woven bone. A complication, however, is that the bone tissue requires highly complex control for regeneration.

WO 01/91663 describes a two-dimensionally oriented bone distraction using an artificial interface. For such distraction methods from the prior art, in many cases only vertical regeneration is possible, for example in the jaw region.

Thus, bone regeneration by distraction cannot be used for every type of bone defect. In addition, the devices used for distraction are complex, and distraction methods take a comparatively long time.

SUMMARY

The technical object of the present invention is to provide a device which allows bone regeneration methods to be carried out which overcome the disadvantages of the prior art. A further technical object of the invention is the provision of devices, use of same, and methods which allow simple and economical bone regeneration. A further technical object of the invention is the provision of devices, use of same, and methods which allow regeneration of bone and which have improved quality and sufficient vascularization.

The technical object is achieved by the present invention in particular by providing devices, methods, and uses according to the claims.

The technical object is achieved by the present invention in particular by providing a device for regenerating a bone, comprising sheathing and a swelling agent enclosed by the sheathing, wherein the sheathing is biocompatible, and is expandable, contractible, and/or deformable in a predefined and controlled manner as a function of a force effect induced by a change in volume of the swelling agent.

The device is a three-dimensional device.

According to the invention, the sheathing is preferably expandable in a predefined and controlled manner as a function of the force effect. According to the invention, the sheathing is preferably deformable in a predefined and controlled manner as a function of the force effect.

According to the invention, the change in volume of the swelling agent as a result of contact with and absorption of liquid, preferably a liquid containing biomolecules and/or cells, particularly preferably blood, is preferably induced by the swelling agent. According to the invention the liquid is preferably water. According to the invention the liquid is preferably a bodily fluid. According to the invention the liquid is preferably an interstitial liquid. According to the invention the liquid is preferably blood. According to the invention, the absorbed liquid preferably contains no solid constituents larger than 150 kDa, particularly preferably larger than 100 kDa, in particular larger than 50 kDa.

Provision of the device according to the invention allows the device to be introduced into a bone defect, for example by surgical means. After introduction into the bone defect, according to the invention the volume of the swelling agent changes, for example increases or decreases, due to contact with a liquid and associated liquid migration, in particular absorption of the liquid. As a result of the change in volume of the swelling agent the sheathing of the device is changed in shape and/or size, particularly preferably the surface and thus the enclosed volume being enlarged. According to the invention, the swelling agent preferably expands and thus presses from the inside against the sheathing. As a result, after introduction of the device, osteogenic cells or cell aggregates which have migrated into the bone defect and adhered to the device, in particular to the sheathing, preferably the outer surface thereof, and/or to preferably provided lamellae, are slowly exposed in a defined manner to stress, i.e., biomechanical stimulus, in particular when they are located at a distance from the device for which distraction is effective. As a result of the defined expansion of the device according to the invention in the bone defect and the associated distraction of cells adhered to the device, a three-dimensional callus distraction is achieved. In this manner a callus precursor is produced in the entire defect all at once by distraction, and then only needs to ossify. This stimulus is advantageously achieved in essentially a large number of cells, particularly preferably in all cells at the same time. According to the invention, biomechanical stimuli may be transmitted directly to the osteoblasts without the need for fibroblasts. Thus, the distraction may act on the osteoblasts with comparatively small forces.

The pulses generated by the motion, in particular expansion, of the device according to the invention may be directly transmitted as a stimulus directly to the osteogenic cells by means of the device or via the body's own fibrin framework. In one alternative embodiment of the invention, the sheathing of the device according to the invention may also have a three-dimensional framework and/or lamellae. In that case, the pulses may also be transmitted to the osteogenic cells via the three-dimensional framework and/or the lamellae.

The device according to the invention may advantageously be used in methods, preferably methods according to the invention, for bone regeneration, in particular for three-dimensional callus distraction.

The present teaching encompasses in particular devices and methods for bone regeneration, wherein preferably bone in the jaw region and/or periodontal region is to be regenerated.

In particular, for the present invention the term "bone regeneration" is also understood to mean the regeneration of bone defects, for example after cystectomy, tumor surgery, or trauma surgery, etc., regardless of the topography, and/or in particular also means the regeneration of minor bone defects, for example those caused by periodontitis.

According to the invention, the device according to the invention preferably transmits biomechanical pulses, in particular expansion stimuli or pressure stimuli, to the cells surrounding the device, so that the cells may be distracted or compressed by distances of at least 0.5 μm, in particular 1 μm, more preferably 2 μm, most preferably 10 μm to preferably 100 μm, very particularly preferably 1000 μm, more particularly preferably 1 cm, most particularly preferably up to 10 cm. Thus, according to the invention the device according to the invention preferably changes in length and/or width by the above-referenced preferred distances. Biomechanical pulses are transmitted to the surrounding cells by virtue of this preferred change in length and/or width of the device according to the invention. For example, cells which adhere to the device at at least two adhesion points are expanded by the change in dimension. However, cells surrounding the device may also experience a pressure pulse as a result of the change in dimension of the device. The pulses may also be relayed via the body's own fibrin network.

According to the invention, the biomechanical pulses are preferably transmitted at a maximum distraction rate of 1 mm/day. According to the invention, the expansion stimuli are preferably transmitted at a maximum distraction rate of 1 mm/day. According to the invention, the pressure stimuli are preferably transmitted at a maximum distraction rate of 1 mm/day.

According to the invention, the device according to the invention is preferably composed of sheathing and a swelling agent. According to the invention, the device according to the invention is preferably composed of sheathing, a swelling agent, and at least one lamella, in particular at least two lamellae.

According to the invention, the swelling agent is preferably situated inside the sheathing, i.e., is enclosed by the sheathing. According to the invention, the sheathing thus preferably forms a cavity in which the swelling agent is situated. According to the invention, preferably a portion of the cavity, in particular the entire cavity, which is formed by the sheathing is filled with the swelling agent. According to the invention, preferably the entire cavity which is formed by the sheathing is filled with the swelling agent. The cavity is delimited by the sheathing, also when the sheathing has openings, for example pores.

According to the invention the device is preferably biodegradable. According to the invention the components of the device, in particular the sheathing and the swelling agent, are preferably biodegradable.

According to the invention, the degradation kinetics of the device, in particular of the sheathing and of the swelling agent, are adapted to the time schedule for a distraction to be carried out using the device according to the invention.

According to the invention the swelling agent is preferably a hydrogel.

According to the invention the swelling agent is preferably solid. According to the invention the swelling agent is preferably semisolid. According to the invention the swelling agent is preferably liquid.

According to the invention the swelling agent, in particular the hydrogel, is present as a powder.

According to the invention the hydrogel is preferably carboxymethylcellulose. According to the invention the hydrogel preferably contains carboxymethylcellulose. According to the invention the hydrogel is preferably composed of a polysaccharide. According to the invention the hydrogel preferably contains at least one polysaccharide. According to the invention the hydrogel is preferably hyaluronic acid. According to the invention the hydrogel preferably contains hyaluronic acid. According to the invention the swelling agent preferably contains various components, in particular mixtures of the components disclosed herein, such as carboxymethylcellulose, polysaccharides, and/or hyaluronic acid.

According to the invention the swelling agent is preferably biocompatible. According to the invention the swelling agent is preferably biodegradable.

According to the invention the swelling agent is preferably nonbiogenic, and in particular contains no collagen, i.e., is collagen-free. According to the invention the swelling agent is preferably biogenic.

In the context of the present invention, the "volume" of the swelling agent is understood to mean the volume that is delimited by the outer surfaces of the swelling agent. According to the invention the swelling agent is preferably delimited by the sheathing. The swelling agent is preferably present in the form of a starting volume, preferably the original starting volume, which is able to change to a different volume as the result of contact with a liquid, in particular as the result of absorption of liquid. A change in the volume means a change in the starting volume, in particular a significant change in the starting volume, preferably an increase in the starting volume. The change may be, for example, a change in the starting volume of at least 1%, preferably 5%, preferably 10%, preferably 15%, preferably 20%, preferably 30%, preferably 40%, preferably 50%, preferably 60%, preferably 70%, preferably 80%, preferably 90%, and in the case of an enlargement, preferably at least 100%, preferably 150%, preferably 200%, or preferably 300%, for example as the result of expansion or deformation of the sheathing.

According to the invention, the change in volume of the swelling agent is preferably an increase in volume.

According to the invention, the material of the sheathing is preferably expandable, contractible, and/or deformable in a predefined and controlled manner as a function of an external force effect. The material may have plastic or elastic properties. These properties of the material of the sheathing enable the capacity, provided according to the invention, of the swelling agent surrounded by the sheathing to reversibly or irreversibly change in volume in a predefined and controlled manner.

According to the invention, the starting volume of the swelling agent preferably changes at a predetermined rate. According to the invention, the maximum rate at which the starting volume of the swelling agent is able to change is great enough that the cells adhering to the device and/or the cells surrounding the device are distracted and/or compressed a maximum of 1.5 mm/day, particularly preferably 1.2 mm/day, in particular 1 mm/day, most preferably 0.9 mm/day.

In one preferred embodiment, the volume of the swelling agent may change in a predefined and controlled manner at a rate at which expansion or contraction of a volume of 1000 $\mu m^3$ to 216,000 $\mu m^3$ occurs at a maximum of 0.6 mm per day in at least one spatial coordinate, particularly preferably a maximum of 0.577 mm per day, in particular a maximum of 0.55 mm per day, most preferably a maximum of 0.5 mm per day. In one preferred embodiment, the volume may change in a predefined and controlled manner at a rate at which expansion or contraction of a volume of 1000 $\mu m^3$ to 216,000 $\mu m^3$ occurs in at least one spatial coordinate at a maximum of at least 0.01 mm per day, particularly preferably at least 0.1 mm per day, in particular at least 0.2 mm per day, most preferably at least 0.5 mm per day.

In one preferred embodiment, the volume of the swelling agent may change in a predefined and controlled manner at a rate at which expansion or contraction of a section of the body diagonals of the volume of the swelling agent between 10 μm and 60 μm in length occurs at a maximum of 0.6 mm per day, particularly preferably a maximum of 0.577 mm per day, in particular a maximum of 0.55 mm per day, most preferably a maximum of 0.5 mm per day. In one preferred embodiment, the volume may change in a predefined and controlled manner at a rate at which expansion or contraction of a section of the body diagonals of the volume of the swelling agent between 10 μm and 60 μm in length occurs at least 0.01 mm per day, particularly preferably at least 0.1 mm per day, in particular at least 0.2 mm per day, most preferably at least 0.5 mm per day.

According to the invention, the device is designed in such a way that the starting volume of the swelling agent is able to change continuously. According to the invention, the device is designed in such a way that the starting volume of the swelling agent is able to change discontinuously.

In the context of the present invention, "in a predefined and controlled manner" is understood to mean a change in the starting volume, in particular an expansion or contraction, which occurs over a predetermined distance and/or a predetermined volume, and whose rate, i.e., the expansion rate, contraction rate, or rate of change in volume, is likewise predetermined, i.e., intentionally selected. According to the invention, a change in the volume may also be only a change in the shape of the volume. According to the invention, the point in time of the expansion, contraction, or start of the change in volume may also preferably be predetermined, i.e., intentionally selected.

According to the invention, the sheathing preferably reacts to the change in volume of the swelling agent by expansion, deformation, and/or contraction. According to the invention, the sheathing preferably reacts to the change in volume of the swelling agent by expansion. According to the invention, the sheathing preferably reacts to the change in volume of the swelling agent by deformation. According to the invention, the sheathing preferably reacts to the change in volume of the swelling agent by expansion and deformation.

In the context of the present invention, "expansion" is understood to mean an enlargement of the sheathing along at least one spatial axis. According to the invention, the enlargement preferably takes place along one spatial axis. According to the invention, the enlargement preferably takes place along two spatial axes. According to the invention, the enlargement preferably takes place along all three spatial axes.

In the context of the present invention, "contraction" is understood to mean a reduction in size of the sheathing along at least one spatial axis, preferably along one spatial axis, two spatial axes, or all three spatial axes.

According to the invention, the sheathing preferably contains a material selected from the group comprising polyglycolic acid, polylactic acid, poly(ε-caprolactone), poly(β-hydroxybutyrate), poly(p-dioxanone), a polyanhydride, or a mixture of same, for example a mixture of polylactic acid and polyglycolic acid. According to the invention the sheathing preferably contains polylactic acid. According to the invention the sheathing preferably contains poly(ε-caprolactone). According to the invention the sheathing preferably contains a carbolactone.

According to the invention, the material of the sheathing preferably contains copolymers, in particular composed of at least two of the above-mentioned materials. According to the invention, the material of the sheathing preferably contains polymer mixtures.

According to the invention, the sheathing is preferably composed of a material selected from the group comprising polyglycolic acid, polylactic acid, poly(ε-caprolactone), poly (β-hydroxybutyrate), poly(p-dioxanone), a polyanhydride, or a mixture of same. According to the invention, the material of the sheathing is preferably composed of copolymers of at least two of the above-mentioned materials.

According to the invention the sheathing is preferably composed of polylactic acid.

Sheathing which contains or is composed of polylactic acid has the advantage that the polylactic acid is degraded into short-chain metabolites. In addition, polylactic acid imparts a certain hardness to the sheathing.

According to the invention the sheathing is preferably composed of poly(ε-caprolactone).

Sheathing which contains or is composed of poly(ε-caprolactone) has the advantage that poly(ε-caprolactone) is particularly biocompatible. In addition, long chains composed of poly(ε-caprolactone) may be formed. Little or no free acids are formed from poly(ε-caprolactone).

According to the invention the sheathing is preferably composed of carbolactone.

According to the invention the sheathing is preferably composed of or contains at least one polymer, preferably a polymer composed of spatially crosslinked polymers.

According to the invention, the material of the sheathing preferably has good processing characteristics. According to the invention the material of the sheathing is preferably sterilizable. According to the invention the device is preferably sterilizable. According to the invention, the material of the sheathing may preferably be adapted satisfactorily to the regeneration geometry. According to the invention, the material of the sheathing and/or of the device preferably has good storage characteristics.

According to the invention, the material of the sheathing preferably is polyglycolic acid or contains same. According to the invention, the material of the sheathing is preferably polylactic acid or contains same. According to the invention, the material of the sheathing is preferably poly(ε-caprolactone) or contains same. According to the invention, the material of the sheathing is preferably poly(β-hydroxybutyrate) or contains same. According to the invention, the material of the sheathing is preferably poly(p-dioxanone) or contains same. According to the invention, the material of the sheathing is preferably at least one polyanhydride or contains same. According to the invention, other suitable materials may also preferably be used. According to the invention, the material of the sheathing is preferably composed of at least one polylactite and at least one polyglycolide. According to the invention, copolymers having different physical and mechanical properties may preferably be produced by the combination and variation of the lactite and glycolide fractions and used as material of the sheathing.

According to the invention, the material of the sheathing preferably has specific rubber-elastic properties and has sufficient mechanical stability to overcome the tissue pressure present in the defect region of the bone. In particular, in one preferred embodiment the material of the sheathing is capable of resisting an effective tissue pressure of up to 9.5 mm Hg in the tissue surrounding same.

According to the invention the sheathing is preferably anisotropic. In the context of the present invention, "anisotropy" is understood to mean the spatial variation in the macroscopic mechanical properties.

According to the invention the sheathing is preferably non-biogenic, and in particular contains no collagen, i.e., is collagen-free. According to the invention the sheathing is preferably biogenic.

According to the invention the sheathing has at least one cell adhesive property; i.e., it is able to bind cells, in particular osteoblasts, fibroblasts, and/or endothelial cells, and preferably is able to bind specifically and selectively. According to the invention, the cell adhesive property of the sheathing is determined by its surface characteristics.

According to the invention the sheathing is preferably biocompatible. According to the invention the sheathing is preferably biodegradable.

According to the invention the sheathing and/or the swelling agent are preferably biodegradable.

In the context of the present invention, "biodegradable" is understood to mean that the material may be degraded or absorbed by hydrolysis, polymer degradation, enzymatic decomposition, and/or dissociation of the material components, preferably in an organism, for example a human or animal organism. According to the invention, the degradation products of the device preferably have a molecular weight of 50,000 g/mol maximum, particularly preferably 40,000 g/mol maximum. Thus, they may be excreted in the normal manner.

According to the invention, the biodegradable device is preferably degraded in an organism within an absorption time of two years, particularly preferably within one year, in particular within one month, most preferably within two weeks.

According to the invention, the absorption preferably begins 6 weeks after the device is introduced into an organism.

According to the invention, the absorption time for the device, in particular of the sheathing and/or of the swelling agent, is at least 4 weeks, particularly preferably at least 8 weeks, in particular at least 16 weeks, most preferably at least 32 weeks. According to the invention, the absorption time for the device is preferably a maximum of 52 weeks, particularly preferably a maximum of 38 weeks, more preferably a maximum of 16 weeks, most preferably a maximum of 8 weeks.

According to the invention the material of the sheathing preferably has a density of 1 to 5 $g/cm^3$. According to the invention the material of the sheathing preferably has rigidity and ductility, and a strength of 1000 to 8000 MPa. According to the invention, the material of the sheathing preferably has a modulus of elasticity of 50 to 500 GPa. According to the invention, the material of the sheathing preferably has an elongation at break of 0.2 to 10%.

According to the invention, before introduction into a defect region of a bone the sheathing is preferably externally coated with cells, in particular endothelial cells and/or osteoblasts and/or fibroblasts.

According to the invention, the material of the sheathing is particularly preferably composed of at least one fiber composite or contains same. According to the invention, the material of the sheathing is particularly preferably composed of fibers of a fiber composite or contains same. According to the invention, the material of the sheathing is preferably optionally encased by a thermoplastic matrix or embedded in same. According to the invention, mechanical protection of the fibers under pressure and shear stress, strength under strain, and protection of the recipient tissue from the integrated fiber particles are thus provided. In particular, the invention optionally provides sealing of the three-dimensional fiber framework surface. The fibers may preferably be embedded in a matrix having, for example, a different layer thickness. According to the invention, fibers of a fiber composite are preferably partly or completely embedded in a polymer matrix in the material of the sheathing.

According to the invention, the properties of the fiber composites, with or without a matrix, may preferably be specified by the fiber volumetric capacity and by the orientation of the fibers in the fiber architecture. In this manner the strength and the modulus of elasticity of the sheathing according to the invention may also preferably be specified according to the invention.

According to the invention the sheathing is preferably coated. According to the invention the sheathing is preferably coated using thin-layer technology. According to the invention the sheathing is preferably coated using vacuum, plasma, or ion technology. Desired protein adsorption may be influenced in a targeted manner using a coating preferred according to the invention. In addition, hemocompatibility may be improved by coating with antithrombogenic surfaces. Cell adhesion to the sheathing and influencing of cell growth of the adhered cells may be achieved in a targeted, controlled manner using a thin coating preferred according to the invention. The electrical properties of the surface of the sheathing may be modified in a targeted manner using a coating preferred according to the invention.

According to the invention, the fibers of a fiber composite may preferably be coated to increase the cell adhesion. According to the invention the fibers are preferably coated with titanium. According to the invention the sheathing is preferably coated with titanium. According to the invention the fibers are preferably coated with titanium oxide. According to the invention the sheathing is preferably coated with titanium oxide. According to the invention the fibers are preferably coated with sodium alginate. According to the invention the sheathing is preferably coated with sodium alginate.

To allow the most effective use possible of the device according to the invention, osteoblasts must be able to bind well to the exterior of the device. As the result of improved adhesion between the sheathing and the osteoblasts, when a device according to the invention is used, in particular in a method according to the invention, more osteoblasts are activated by the device by means of one or more biomechanical pulses. For this reason, the sheathing or the coating of the sheathing is preferably designed according to the invention in such a way that optimum osteoblast binding to the sheathing can take place. According to the invention, the adhesion binding of the osteoblasts to the sheathing is preferably so strong that the binding is maintained during a portion of the volumetric expansion, particularly preferably during the entire volumetric expansion, of the swelling agent, in particular when the device is used in a method according to the invention.

According to the invention the material of the sheathing is preferably smooth. According to the invention the coating of the sheathing is preferably smooth. According to the invention the material of the sheathing is preferably rough. According to the invention the coating of the sheathing is preferably rough. A larger surface is available for binding of the osteoblasts by use of a preferred rough surface according to the invention.

According to the invention the sheathing is preferably coated with hydroxyapatite. A coating with hydroxyapatite preferred according to the invention allows adsorption of proteins, which promotes binding.

According to the invention the sheathing is preferably coated with a hydrogel. According to the invention the hydrogel layer is preferably thin.

According to the invention the sheathing is preferably coated with at least one protein. According to the invention the at least one protein contains the amino acid sequence Arg-Gly-Asp, i.e., RGD. According to the invention the sheathing is preferably coated with at least one peptide. According to the invention the at least one peptide is preferably a peptide which initiates the cell adhesion. According to the invention the at least one peptide is preferably an RGD peptide. According to the invention the at least one peptide is preferably synthetically produced. According to the invention the at least one peptide preferably contains the amino acid sequence Arg-Gly-Asp, i.e., RGD. According to the invention the at least one peptide preferably comprises the amino acid sequence Arg-Gly-Asp, i.e., RGD.

According to the invention the sheathing is preferably coated with star-shaped polyethylene glycol polymers (star PEG).

According to the invention, the at least one protein is preferably bound, particularly preferably covalently bound, to the polyethylene glycol polymer coating. According to the invention, the at least one peptide is preferably bound, particularly preferably covalently bound, to the polyethylene glycol polymer coating.

The adhesion of osteoblasts is a receptor-mediated contact between the molecules of the extracellular matrix and the actin fibers of the cytoskeleton. This region is also referred to as the focal contact zone. Molecules which provide for binding as well as molecules which are responsible for signal transduction are present in the focal contacts. Formation of the focal adhesion is caused primarily by integrins. The integrins differ from other cell surface receptors by virtue of their bioaffinity. Adhesion proteins in the form of an ultrathin coating on the sheathing facilitate the adhesion binding of osteoblasts to the device according to the invention. Fibronectin is an extracellular adhesion protein having multiple specific binding sites for receptors, and is therefore used for binding the osteoblasts to the extracellular matrix. Fibronectin is a large glycoprotein, which as a dimer is composed of two essentially identical subunits. Fibronectin is composed of approximately 90 amino acids. The cell-binding site of fibronectin has been identified as the tripeptide sequence Arg-Gly-Asp (RGD).

According to the invention, the sheathing is composed of a fiber composite made of continuous fibers, or contains same. According to the invention, the sheathing is preferably composed of a fiber composite made of differently oriented layers. According to the invention, the layer sequence of the fibers may preferably be symmetrical to the center plane of the sheathing, or may be configured randomly or in intermediate stages thereof. According to the invention, fibers of a fiber composite preferably represent the primary load-bearing element of the sheathing having a thermoplastic matrix. Because of their higher modulus of elasticity and higher strength, the fibers largely determine the mechanical properties of the composite.

According to the invention, the device and in particular the sheathing are characterized by their biofunctionality. The physical, mechanical, and/or biological properties in conjunction with the time-related biomechanical stimulus emission are important for biofunctionality.

According to the invention, the surface of the sheathing is preferably chemically modified. According to the invention, the surface of the sheathing is preferably chemically modified by reactive molecules or groups of molecules. According to the invention, the molecules or groups of molecules by means of which the surface of the sheathing is chemically modified are preferably able to react with anchor proteins of the extracellular matrix of cells. According to the invention the surface of the sheathing is preferably hydrophilic. Hydrophilic surfaces allow better adhesion for cells than do hydrophobic surfaces.

According to the invention the sheathing preferably has a thickness of at least 0.01 mm. According to the invention the sheathing preferably has a maximum thickness of 1 mm. According to the invention the sheathing preferably has a thickness of at least 0.05 mm and a maximum thickness of 0.5 mm. According to the invention the sheathing preferably has a thickness of approximately 0.1 mm.

According to the invention the sheathing is preferably permeable to a liquid. According to the invention the sheathing is preferably permeable to water. According to the invention the sheathing is preferably porous. According to the invention the sheathing preferably has pores which are permeable to water and to solids, for example proteins and sugars having a mass of less than 100 kDa, particularly preferably less than 50 kDa. According to the invention the sheathing preferably has pores which are nonpermeable to solids, for example proteins and sugars having a mass of greater than 50 kDa, particularly preferably greater than 100 kDa, in particular greater than 150 kDa. According to the invention, the pores preferably have a size of 2 µm maximum, particularly preferably 1 µm maximum. According to the invention, the pores preferably have a size of 0.5 µm maximum, particularly preferably 0.1 µm maximum. According to the invention, the pores preferably have a size of at least 0.01 µm, particularly preferably at least 0.05 µm. According to the invention, the pores preferably have a size of at least 0.1 µm, particularly preferably at least 0.5 µm. According to the invention, the pores preferably have a size of 1 µm.

The pores allow penetration of a liquid through the sheathing and into the device, to the swelling agent. The liquid which penetrates into the device induces a change in volume, in particular an increase in volume, of the swelling agent.

According to the invention the pores are preferably open. However, according to the invention the pores may also preferably be closed, using an absorbable film. The absorbable film is preferably closed against concentration gradients. According to the invention, the absorbable film is preferably absorbed, in particular quickly absorbed, during use of the device so that a liquid is able to pass through the pores and into the device.

According to the invention the sheathing preferably completely encloses the swelling agent. The sheathing may, for example, form a capsule around the swelling agent. However, the sheathing may also be tubular, with each end closed, for example clamped.

According to the invention, the sheathing preferably does not completely enclose the swelling agent; i.e., the sheathing partially encloses the swelling agent. The sheathing may, for example, form a tubular shape which is open at one or both ends, and in which the swelling agent is situated.

According to the invention the sheathing preferably determines the shape of the device.

According to the invention the sheathing preferably has a length and/or width of up to 10 mm. According to the invention, the sheathing preferably has a length and/or width of 0.1 to 10 mm, in particular 0.5 mm to 5 mm, particularly preferably 1 mm to 2 mm. Alternatively, however, it may be provided that the sheathing is less than 1 mm in length and/or width. However, it may also be alternatively provided that the sheathing is greater than 10 mm in length and/or width.

According to the invention the sheathing preferably has the shape of a tube. According to the invention the sheathing is preferably tubular.

According to the invention the tube formed from the sheathing is preferably straight.

According to the invention, the tube formed from the sheathing preferably forms a ring by joining its two ends together. Tubes formed in a ring shape in this manner may also optionally be linked to one another.

According to the invention the tube preferably has a diameter of 0.5 mm to 5 mm. According to the invention the tube preferably has a diameter of at least 0.5 mm. According to the invention the tube preferably has a diameter of 1 mm to 3 mm. According to the invention the tube preferably has a diameter of 1 mm to 2 mm. According to the invention the tube preferably has a diameter of 2 mm. According to the invention the tube preferably has a diameter of 3 mm. The tube may also have different diameters, in particular diameters preferred according to the invention, in the longitudinal distribution.

According to the invention the tube preferably has a length of 0.5 cm to 15 cm. According to the invention the tube preferably has a length of 0.5 cm to 5 cm. According to the invention the tube preferably has a length of 1 cm to 2 cm. According to the invention the tube preferably has a length of 5 cm to 10 cm. According to the invention the tube preferably has a length of at least 1 cm. According to the invention the tube preferably has a length of 10 cm. According to the invention the tube preferably has a length of greater than 10 cm.

The sheathing, in particular when it has a tubular shape, may alternatively be designed as a hose having a length greater than 5 cm, in particular greater than 10 cm. If necessary, the hose may be divided into individual longitudinal sections having a desired length in order to use the device for distraction.

According to the invention the length of the tube preferably refers to the initial state.

According to the invention, the tube preferably elongates as a result of the increase in volume of the swelling agent. According to the invention, the tube preferably elongates by a factor of approximately 1.5 to 3 as a result of the increase in volume of the swelling agent. According to the invention, the tube preferably elongates by approximately a factor of two as a result of the increase in volume of the swelling agent.

According to the invention, a tube which is originally 1 cm long is 1.5 to 3 cm long, in particular approximately 2 cm long, after use as a result of the increase in volume.

According to the invention the sheathing preferably has the shape of a capsule. According to the invention the sheathing is preferably capsule-shaped.

Suitable capsule shapes are known to one skilled in the art. According to the invention the capsule is preferably composed of one part. According to the invention the capsule is preferably composed of two parts, in particular two halves, which are pushed one inside the other in a known manner.

According to the invention the capsule preferably has a cuboidal, in particular a cubic, shape. According to the invention the capsule is preferably round, for example ovoid or torpedo-shaped. According to the invention the capsule preferably has an ellipsoidal or a spherical shape.

According to the invention the capsule-shaped sheathing preferably forms a macrocapsule. According to the invention the macrocapsule preferably has a volume of 0.5 cm$^3$ to 2 cm$^3$, particularly preferably approximately 1 cm$^3$, in particular 1 cm$^3$. According to the invention the volume of the macrocapsule preferably refers to the initial state.

According to the invention the macrocapsule in the form of a cube preferably has a side length of 1 cm.

According to the invention at least one side, in particular one side, of the macrocapsule elongates as a result of the increase in volume of the swelling agent. According to the invention, the at least one side of the macrocapsule elongates by a factor of approximately 1.5 to 3 as a result of the increase in volume of the swelling agent. According to the invention, the at least one side of the macrocapsule elongates by a factor of approximately two as a result of the increase in volume of the swelling agent.

According to the invention the capsule-shaped sheathing preferably forms a macrocapsule. According to the invention the macrocapsule preferably has a volume of 0.5 mm$^3$ to 3 mm$^3$, particularly preferably approximately 1 mm$^3$, in particular 1 mm$^3$. According to the invention the volume of the macrocapsule preferably refers to the initial state.

According to the invention, the macrocapsule in the form of a cube preferably has a side length of 0.5 mm to 3 mm, in particular 1 mm to 2 mm.

According to the invention, the macrocapsule in the form of a sphere or ellipsoid preferably has a diameter of 0.5 mm to 3 mm, in particular 1 mm to 2 mm.

According to the invention the side length and the diameter of the macrocapsule preferably refer to the initial state.

As previously mentioned, according to the invention the change in volume of the swelling agent may preferably cause a deformation of the sheathing. According to the invention, the sheathing may preferably have certain sections or parts which allow deformation, in particular targeted deformation. For example, such a section or part of the sheathing may have the accordion-like shape of a bellows or corrugated hose.

According to the invention, at least one part of the sheathing preferably has the shape of a bellows.

According to the invention, at least one part of the sheathing preferably has the shape of a corrugated hose.

According to the invention, the sheathing preferably has the shape of a bellows.

In one alternative embodiment according to the invention, the sheathing, in particular when it is tubular or capsule-shaped, may have multiple sections which have the shape of a bellows or a corrugated hose. In particular for fairly long sheathings, for example having a length of greater than 1 cm or even 10 cm and greater, multiple sections in the shape of a bellows or a corrugated hose may be provided.

According to the invention the sheathing preferably has the shape of a corrugated hose.

According to the invention the tubular sheathing preferably has the shape of a bellows or corrugated hose.

The part of the sheathing shaped as a bellows or corrugated hose may be pulled apart or pushed together in the same way as for the similar part of a flexible drinking straw.

The bellows or corrugated hose is preferably composed of at least one, particularly preferably at least two, in particular a plurality, of folds.

According to the invention, the folds of the bellows or corrugated hose preferably have a length of 0.5 mm to 2 mm, calculated from the inner circumference of the sheathing to the distal end of the folds, which in a manner of speaking form the outer circumference. According to the invention, the folds of the bellows or corrugated hose preferably have a length of 1 mm.

According to the invention, the at least one part of the sheathing shaped as a bellows or corrugated hose is preferably pushed together in the initial state, i.e., before use of the device according to the invention. The preferably at least one part of the sheathing shaped as a bellows or corrugated hose is pushed apart as a result of the change in volume, in particular the increase in volume, of the swelling agent.

According to the invention, at least one bellows or corrugated hose is preferably provided in a capsule-shaped embodiment of the sheathing.

According to the invention, at least one bellows or corrugated hose is preferably provided in a tubular embodiment of the sheathing.

During use of the device the bellows or corrugated hose is pushed apart as a result of the increase in volume, resulting in a change in shape of the sheathing, in particular resulting in an elongation of a tubular or capsule-shaped sheathing.

However, the change in shape or change in size of the sheathing may also be brought about by expansion or contraction of the sheathing.

According to the invention, the swelling agent preferably pushes the tubular sheathing apart only in the longitudinal direction, in particular with the aid of at least one bellows or corrugated hose. According to the invention, the sheathing, in particular tubular sheathing, does not undergo bulging as a result of the change in volume of the swelling agent.

According to the invention the outer surface of the sheathing is enlarged, in particular as the result of providing contours. This enlargement not only increases the surface that is available to the cells, but also influences the organization of cellular growth.

In one preferred alternative embodiment according to the invention, the outer surface of the sheathing is enlarged by means of a grid-like framework. The framework may enclose the sheathing completely or at least partially. The framework may be connected to the sheathing, and in particular may be mounted on the sheathing. The framework may thus also be a component of the sheathing. The framework material may, for example, be a material which is suitable for the sheathing. In one particular embodiment the framework material may be the same material as that used for the sheathing. Upon a change in volume, in particular an increase in volume, of the sheathing the volume of the space enclosed by the framework therefore also changes. The framework may form a three-dimensional grid which transmits the pulses from the sheathing undergoing a change, in particular an increase, in volume to the osteogenic cells adhering to the grid.

According to the invention, the outer surface of the sheathing is preferably enlarged by means of lamellae. In one preferred embodiment of the present invention the lamellae have rod- or tube-like projections. In another particularly preferred embodiment the lamellae have planar projections, in particular wall-, plate-, leaf-, fan-, or wing-like or otherwise planar projections. In a further preferred embodiment the lamellae have enlarged surfaces, in particular as the result of lamellae substructures, branches, protuberances, or meshlike structures.

According to the invention the exterior of the sheathing preferably bears at least one lamella. According to the invention the exterior of the sheathing preferably bears at least two lamellae. According to the invention the exterior of the sheathing preferably bears a plurality of lamellae. According to the invention the exterior of the sheathing preferably bears 2 to 20 lamellae.

According to the invention, the at least one lamella may preferably be a component of the sheathing. According to the invention, the at least one lamella is preferably composed of the same material as the sheathing.

According to the invention, the at least one lamella is preferably not a component of the sheathing. According to the invention, the at least one lamella is preferably composed of a different material than the sheathing.

According to the invention, the at least one lamella is preferably part of a tubular sheathing. According to the invention, the at least one lamella is preferably part of a capsule-shaped sheathing.

According to the invention the at least two lamellae are preferably parallel to one another.

According to the invention the at least one lamella is preferably rigid.

According to the invention the at least one lamella preferably has a circular cross section. According to the invention the at least one lamella preferably has a rectangular cross section. According to the invention the at least one lamella preferably has a square cross section. However, the at least one lamella may also have any other geometric shape, for example an oval or polygonal cross section.

According to the invention, the at least one lamella preferably encloses the sheathing in such a way that the sheathing lies in the middle of the lamellar face. Thus, the lamella encloses the entire circumference of the sheathing, and extends away from same in the distal direction.

According to the invention the at least one lamella preferably has a side length of 0.2 to 2 cm. According to the invention the at least one lamella preferably has a side length of 0.5 to 1 cm. According to the invention the at least one lamella preferably has a side length of 1 cm.

According to the invention the at least one lamella preferably has a diameter of 0.2 to 2 cm. According to the invention the at least one lamella preferably has a diameter of 0.5 to 1.5 cm. According to the invention the at least one lamella preferably has a diameter of 1 cm.

According to the invention the at least one lamella preferably has a thickness of 0.05 mm to 0.5 mm. According to the invention the at least one lamella preferably has a thickness of 0.1 mm to 0.3 mm. According to the invention the at least one lamella preferably has a thickness of 0.2 mm.

According to the invention the at least one lamella preferably has no pores.

According to the invention the at least one lamella preferably has pores. Thus, the at least one lamella is preferably perforated according to the invention. According to the invention the pores preferably have a diameter of 0.5 to 2 mm, particularly preferably approximately 1 mm, in particular 1 mm.

According to the invention the sheathing preferably has no lamellae.

In one preferred alternative embodiment of the invention, two, multiple, or a large number of devices according to the invention, comprising sheathing and a swelling agent enclosed by the sheathing, may be connected to one another via a framework and/or via lamellae. Thus, two, three, four, five to ten, more than ten, or a large number of devices according to the invention may be connected to one another via a framework, for example a grid. However, two, three, four, five to ten, more than ten, or a large number of devices according to the invention may also be connected to one another via multiple lamellae. In particular, at least two devices according to the invention may be connected to one another via a framework, for example a grid. However, at least two devices according to the invention may also be connected to one another via one or more lamellae. The invention therefore also relates to a device for regenerating a bone, comprising at least two of the above-described devices, the at least two devices being connected to one another via at least one lamella. The invention therefore also relates to a device for regenerating a bone, comprising at least two of the above-described devices, the at least two devices being connected to one another via a framework, in particular a grid.

According to the invention, a plurality of devices may also preferably be present in the form of a granulate. The base units of the granulate, i.e., the individual devices, have an identical or similar design, but are not combined in a superstructure. According to the invention, the individual granulate particles i.e., the individual devices, are fixed to one another using a biodegradable adhesive, and in this manner may be incorporated into the defect.

The invention further relates to the provision of a method for manufacturing a device according to the invention, wherein sheathing is formed from at least one biocompatible material, and before, during, or after the sheathing is formed a swelling agent is introduced into the sheathing, the sheathing being deformable, expandable, and/or contractible in a controlled manner as a function of a force effect.

According to the invention, the swelling agent is preferably introduced after the sheathing is formed.

According to the invention the swelling agent is preferably filled in powdered form.

According to the invention the material of the sheathing is preferably nonbiogenic.

According to the invention the sheathing is preferably closed off, in particular by clamping, after the swelling agent is introduced.

The invention further relates to the use of a biocompatible material which is deformable, expandable, and/or contractible in a predefined and controlled manner as a function of an internal or external force effect and which has a cell adhesive property, for manufacturing a device comprising sheathing composed of the biocompatible material, and a swelling agent which is enclosed by same, for regenerating a bone, wherein the device may be or is introduced into a defect region of a bone.

The invention further relates to the use of a biocompatible material which is deformable, expandable, and/or contractible in a predefined and controlled manner as a function of an external force effect, for manufacturing a device comprising sheathing composed of the biocompatible material, and a swelling agent which is enclosed by the sheathing, for regenerating a bone, wherein the device is introduced into a defect region of a bone. According to the invention the material preferably has a cell adhesive property.

The invention further relates to the use of a device according to the invention or a granulate according to the invention for manufacturing a kit for bone regeneration. According to the invention, the referenced kits preferably contain at least one surgical instrument, particularly preferably at least one applicator, for example a syringe, and a capsule for absorption of the device, for example the device in granulate form. According to the invention the kit preferably contains an instruction manual. According to the invention the kit preferably contains a package, particularly preferably a package which allows sterile storage of the device. According to the invention the kit preferably contains an adhesive, in particular an adhesive for fixing the device in a bone defect.

The invention further relates to a method for regenerating a bone, wherein at least one device, comprising sheathing and a swelling agent which is enclosed by the sheathing, wherein the sheathing is biocompatible and is expandable and/or contractible in a predefined and controlled manner as a function of a force effect, and wherein the force effect is induced by a change in volume of the swelling agent, is introduced into a defect region of a bone, and the sheathing is exposed to a force effect as the result of a change in volume of the swelling agent.

The invention also achieves its technical object, and therefore further relates to the provision of a method for regenerating a bone, wherein at least one previously referenced device according to the invention, comprising sheathing and a swelling agent which is enclosed by the sheathing, is introduced into a defect region of a bone, wherein the sheathing is biocompatible and is expandable and/or contractible in a predefined and controlled manner as a function of a force effect, and has a cell adhesive property, in particular for osteoblasts, fibroblasts, and/or endothelial cells, and the force effect is induced by a predefined and controlled change in volume of the swelling agent.

Accordingly, within the scope of the method according to the invention for bone regeneration, in one preferred embodiment a device, in particular a device according to the invention, is introduced into a defect region of a bone. In this defect region the device is enclosed by a blood clot; i.e., the sheathing of the device contacts the autologous cells contained in the blood clot. After the device has been introduced into the defect region of a bone, a change in volume, i.e., in particular a decrease or increase in volume, of the swelling agent is induced as the result of a liquid. This results in expansion and/or change in shape, and thus, the desired biomechanical stimulation of the attached osteogenic cells, and thus results in distraction and therefore bone regeneration. According to the invention, the force effect preferably occurs within the body, in particular within the bone defect.

According to the invention, the change in volume of the swelling agent may lie in various ranges. The volume change is preferably approximately 10% of the longitudinal expansion of the cells or cell groups adhering to the device.

According to the invention, the change in the expansion distance is preferably at least 0.5 µm, particularly preferably at least 1 µm, more preferably at least 10 µm, even more preferably at least 100 µm, very preferably at least 1000 µm, very particularly preferably at least 10 mm, and most preferably at least 100 mm.

According to the invention, the change in the expansion distance is preferably 100 mm maximum, particularly preferably 10 mm maximum, more preferably 1000 µm maximum, even more preferably at least 100 µm maximum, very preferably 10 µm maximum, very particularly preferably 1 µm maximum, and most preferably 0.5 µm maximum.

According to the invention the distraction distance is preferably 5 mm to 10 mm.

According to the invention, the distraction force of the device must preferably be greater than the contraction force of the fibrin framework or of the blood clot.

According to the invention, the distraction resulting from the deformation, expansion, or contraction of the device preferably begins one day after the device is introduced into the bone defect. According to the invention, the distraction resulting from the deformation, expansion, or contraction of the device preferably begins one week after the device is introduced into the bone defect.

The beginning of the distraction may be predetermined and therefore controlled, for example by virtue of the absorption rate of closures of the pores in the sheathing, for example by using absorbable films.

According to the invention, the distraction preferably takes place over a period of several days, in particular over a period of 5 to 20 days, particularly preferably over a period of approximately 10 days, in particular 10 days.

According to the invention, the rate of change of the volume is at least great enough that cells adhering to the device are distracted at least 1 µm/day. According to the invention, the maximum rate of change of the volume is great enough that cells adhering to the device are distracted between 0.5 mm/day and 1 mm/day. According to the invention, the maximum rate of change of the volume is great enough that cells or osteogenic, callus-producing tissue adhering to the device are distracted a maximum of 1 mm/day. A more rapid distraction rate than 1 mm/day results in differentiation of connective tissue instead of bone. As a result of the change in volume, the device transmits to the cells contained in the blood clot and adhered to the device biomechanical stimuli which trigger the body's own regenerative forces, thereby forming new autologous bone material. This new bone material does not differ from the original bone material surrounding the defect. The change in volume of the device results in biomechanical stimulus transmission throughout the entire space occupied by the device, so that a biomechanical stimulus is transmitted to a much larger number of cells than for distraction osteogenesis from the prior art. According to the invention, the biomechanical stimulus is preferably transmitted from the device directly to osteoblasts.

For a distraction according to the invention, the biomechanical stimuli according to the invention may preferably be transmitted not only directly to osteoblasts adhering to the device, but also indirectly via fibroblasts. According to the invention, fibroblasts adhering to the device preferably further transmit the distraction stimulus to osteoblasts in a metered manner. Without being bound to theoretical aspects, after completion of the distraction the fibroblasts in the so-called "null zone" also become osteoblasts and likewise form bone. For a decreasing distraction rate, the number of fibroblasts preceding the osteoblasts changes.

In contrast, distraction osteogenesis from the prior art transmits biomechanical stimuli via a two-dimensional interface composed of bone or another material only to cells which directly contact this two-dimensional interface.

Thus, the invention provides a method in which a device is introduced into a bone defect, and the device in the bone defect changes in volume and/or shape. As a result of the change in volume and/or shape, biomechanical stimuli are transmitted to cells, in particular osteoblasts, present on the outer surface of the device, thereby stimulating the cells to form bone. The device thus transmits biomechanical stimuli for utilization of the body's own regenerative forces.

The method according to the invention is therefore a three-dimensional distraction. In the context of the present invention, "three-dimensional distraction" is understood to mean distractive bone regeneration in which biomechanical stimuli are transmitted to a bone fragment not only at the interface, i.e., in two dimensions, but also throughout a given volume, i.e., in three dimensions.

According to the invention it may preferably be provided that the distraction occurs along one spatial axis. This may be achieved, for example, by using a device preferred according to the invention having a tubular shape, in which the length of the tube is changed by a bellows, for example.

The method according to the invention uses the body's own healing mechanisms as a bioreactor. Thus, the bone formation occurs under natural conditions, so that the necessary aspects such as growth factors, hormones, and cell composition are implicitly taken into account. In this manner the method according to the invention overcomes problems which may arise as a result of the highly complex control for bone regeneration, as well as the problems of a slow and complicated bone regeneration process using distraction methods from the prior art.

According to the invention, the bone defect is preferably revivified before the device according to the invention is introduced. According to the invention, in the method according to the invention before the device according to the invention is introduced into a bone defect this defect is preferably surgically revivified, and in particular bleeding is induced. A blood clot forms in the defect as a result of the surgical revivification and the induced bleeding.

After the surgical revivification of the bone defect, according to the invention a device according to the invention is preferably introduced into the bone defect. The device is enclosed, in particular completely enclosed, by the blood clot which forms. The swelling agent of the device according to the invention preferably comes into contact with a liquid, for example the blood in the blood clot.

According to the invention, the at least one device is introduced into a defect region of a bone in such a way that the swelling agent comes into contact with a liquid.

According to the invention, the swelling agent thus preferably changes in volume after a defined point in time. According to the invention, the swelling agent preferably changes in volume after one day. According to the invention, the swelling agent preferably changes in volume after one week. Without being bound to theoretical aspects, the blood clot does not contract, but instead enlarges corresponding to the increase in volume of the swelling agent. The cells activated by the device may be converted to proliferating osteoblasts which produce the extracellular matrix, and a callus may be formed which subsequently ossifies. When the device according to the invention is preferably biodegradable, the device is subsequently absorbed and/or metabolized. Thus, the bone defect may be filled with bone tissue which according to the invention is preferably produced by the described biomechanical stimuli from the device. According to the invention, artificially introduced bone replacement materials, growth factors, and other substances besides the device may preferably be dispensed with. According to the invention, the newly formed bone material preferably does not differ, either histologically or in its biological or medical value, from the original bone which surrounds it.

According to the invention, the absorption time of the device is approximately 1 to 2 years, particularly preferably approximately 1.5 years, in particular 1.5 years.

Since the device according to the invention is preferably biodegradable, the space resulting from the degradation of the device may be used for the extracellular matrix. According to the invention, the degradation of the device may preferably be adjusted in such a way that after a few weeks the device degrades after it has emitted the biomechanical stimuli, and the resulting space is occupied by the extracellular matrix.

According to the invention, within the scope of the method according to the invention a device is preferably used whose sheathing has cell adhesive properties. The surface of the sheathing particularly preferably has cell adhesive properties. The surface of the sheathing plays a role in the growth of cells from the blood clot. An adhesion of the cells to the sheathing preferred according to the invention may be influenced by virtue of the surface chemistry, surface physics, and surface topography of the sheathing. According to the invention the surface of the sheathing is preferably hydrophilic. For the ingrowing cells, the interaction between the negatively charged cell membrane and the electrical properties of the surface of the sheathing is preferred according to the invention.

According to the invention, a biodegradable device is preferably introduced into the defect region of a bone. According to the invention, the absorption of the device preferably begins 6 weeks after the device is introduced into a defect region of a bone.

In another embodiment the invention relates to a further method according to the invention for bone regeneration, in particular a further three-dimensional distraction method, in particular an above-referenced device being introduced into a defect region of a bone and moved at that location. In this defect region the device is enclosed by a blood clot; i.e., the surfaces of the device contact the autologous cells contained in the blood clot. Since the device has a three-dimensional structure, the surface of the device is able to come into contact with the autologous cells contained in the blood clot in the entire space that is filled by the device. After the device has been introduced into the defect region of a bone the device is moved within the bone defect. The motion takes place in a controlled and directed manner, i.e., in a predefined direction at a defined rate. As a result of the motion, the device transmits to the cells contained in the blood clot and adhered to the device biomechanical stimuli which trigger the body's own regenerative forces, thus causing new autologous bone material to form. This new bone material does not differ from the original bone material surrounding the defect. The motion of the device results in biomechanical stimulus transmission throughout the entire space defined by the device, so that a biomechanical stimulus is transmitted to a much larger number of cells than for distraction osteogenesis from the prior art.

Thus, the invention provides a method in which a device according to the invention is introduced into a bone defect, and the device is moved in the bone defect. In this embodiment a change in volume of the swelling agent is not necessary, but is possible. As a result of the motion, biomechanical stimuli are transmitted to cells, in particular osteoblasts, which are present on the sheathing of the device, and the cells are thereby stimulated to form bone. The device thus transmits biomechanical stimuli for utilization of the body's own regenerative forces.

According to the invention, a method for regenerating a bone is preferred in which at least one device according to the invention is introduced into a defect region of bone, wherein the device is biocompatible and the sheathing has a cell adhesive property, and after introduction into the defect region the device is moved in the bone defect in a predefined and controlled manner as a function of a force effect.

According to the invention, the device is preferably moved at a rate of at least 1 μm/day and/or 1.5 mm per day maximum, particularly preferably 1 mm per day maximum. According to the invention the motion is preferably carried out continuously or discontinuously.

According to the invention, a biodegradable device is preferably introduced into the defect region of a bone. According to the invention, the absorption of the device begins 6 weeks after the device is introduced into a defect region of a bone.

According to the invention, in the method the volume of the swelling agent preferably does not change during motion of the device.

According to the invention, the method according to the invention for stimulus transmission via a change in volume of the swelling agent of a device according to the invention may preferably be combined with the method according to the invention for stimulus transmission via motion of a device. The disclosed preferred features of the method according to the invention for stimulus transmission via a change in volume are in particular also preferred features of the method according to the invention for stimulus transmission via motion.

According to the invention, the motion of the device may preferably be carried out by means of at least one externally supplied force. According to the invention, the force is preferably introduced using a tension cable or tension rod. According to the invention the supplied force is preferably ultrasound. According to the invention the force is preferably supplied by a magnet.

Further advantageous embodiments of the invention result from the subclaims. The invention is explained in greater detail with reference to the following exemplary embodiment and the accompanying figures.

DRAWINGS

FIG. 1 shows a kit comprising devices in an applicator in the form of a syringe.

Figure 2:
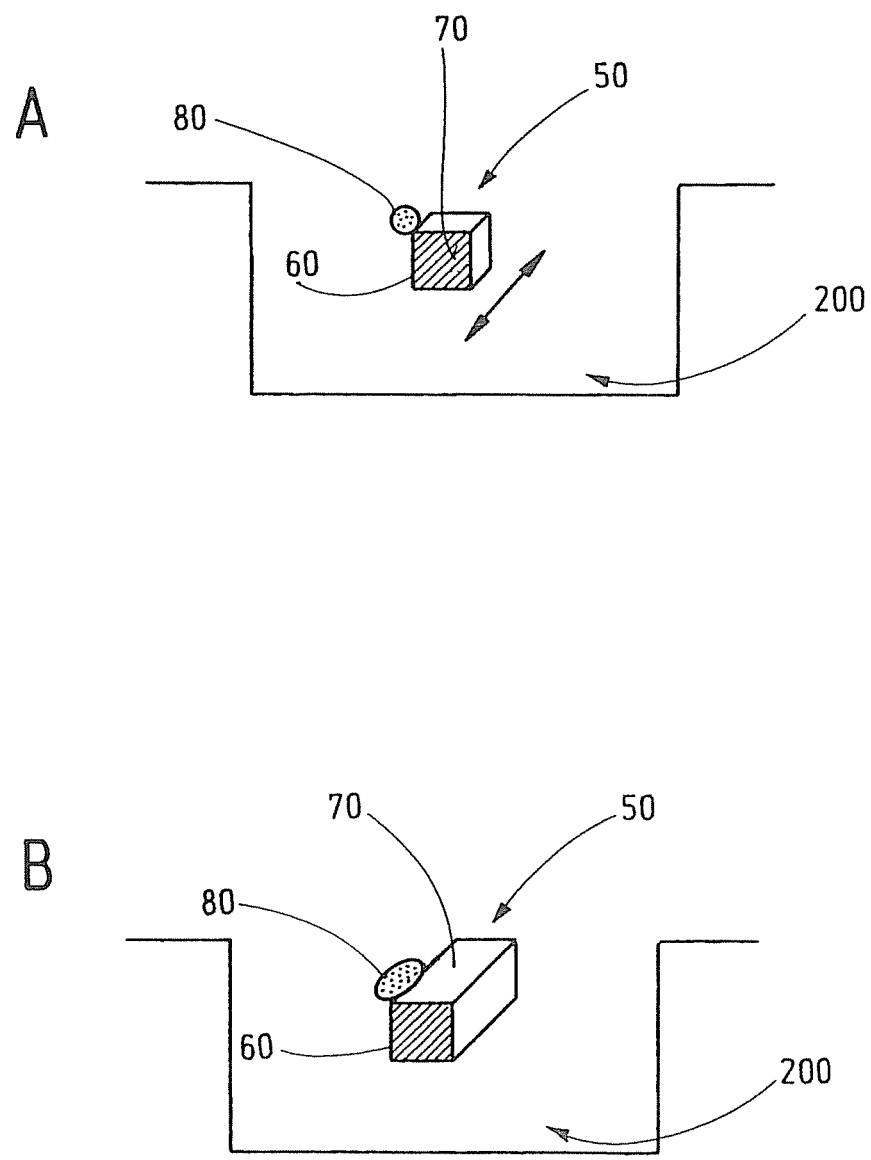

FIG. 2 schematically shows a device which is introduced into a bone defect, before and after the change in volume of the swelling agent contained in the device.

Figure 3:
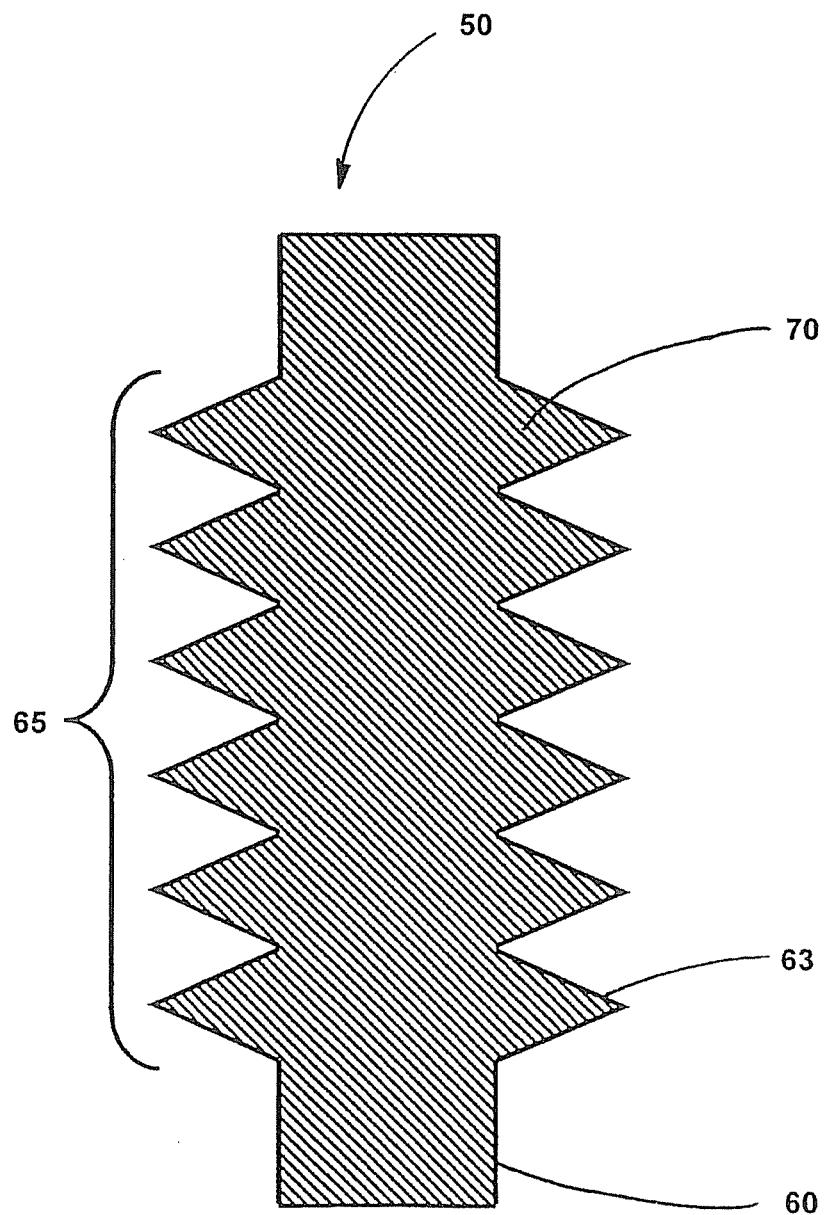

FIG. 3 schematically shows one preferred embodiment of a device according to the invention, without lamellae.

Figure 4:
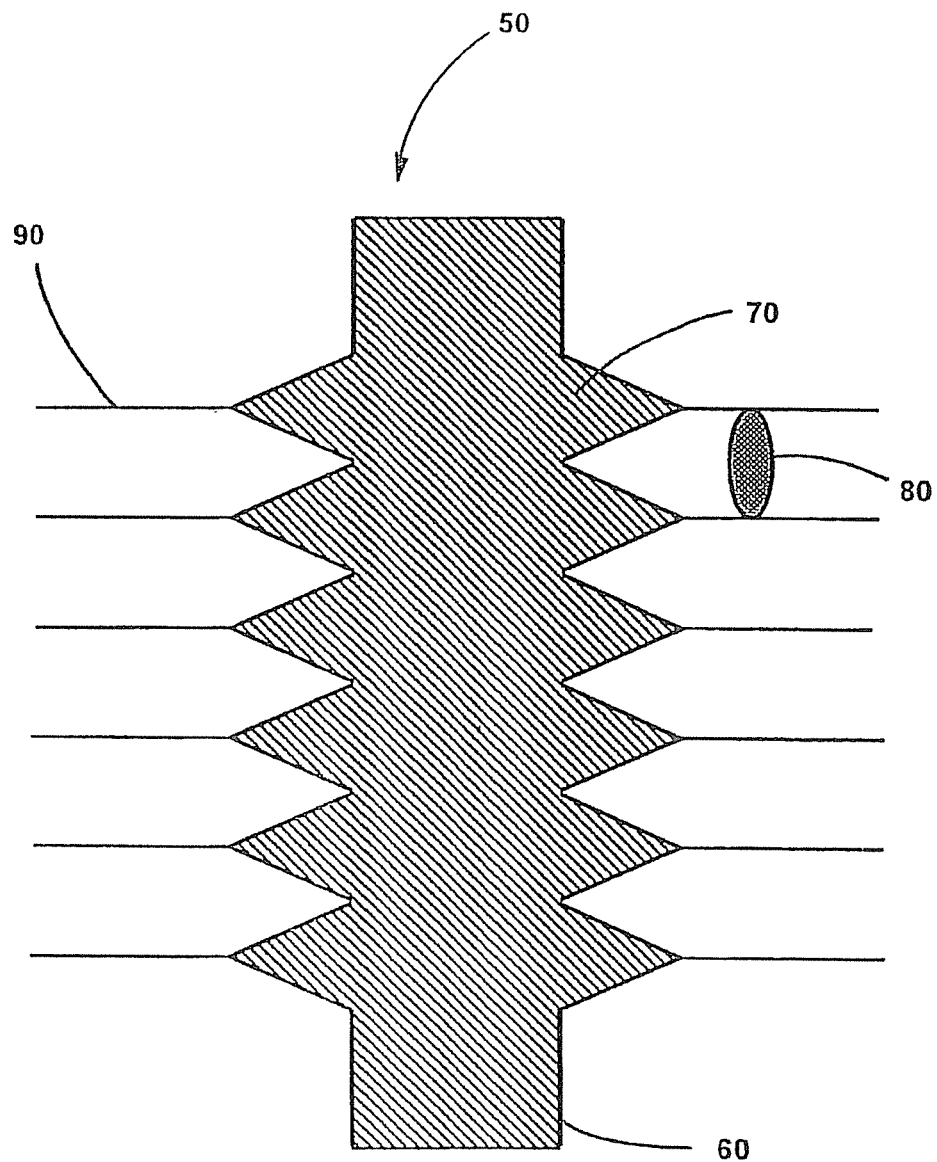

FIG. 4 schematically shows one preferred embodiment of a device according to the invention, with lamellae.

FIG. 5 schematically shows one preferred embodiment of a device according to the invention having planar lamellae, before and after the change in volume of the swelling agent contained in the device.

Figure 6:
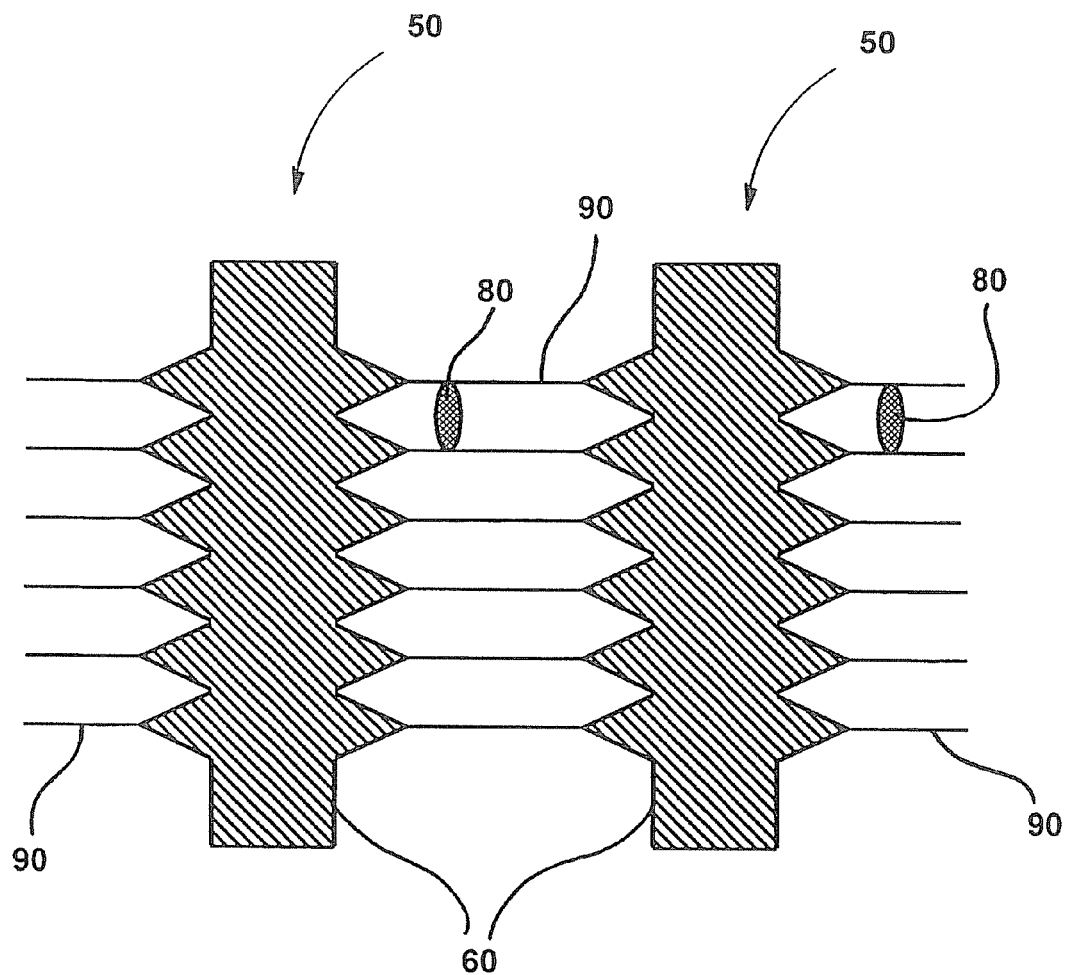

FIG. 6 schematically shows one preferred embodiment of two devices according to the invention which are connected to one another via lamellae.

Figure 7:
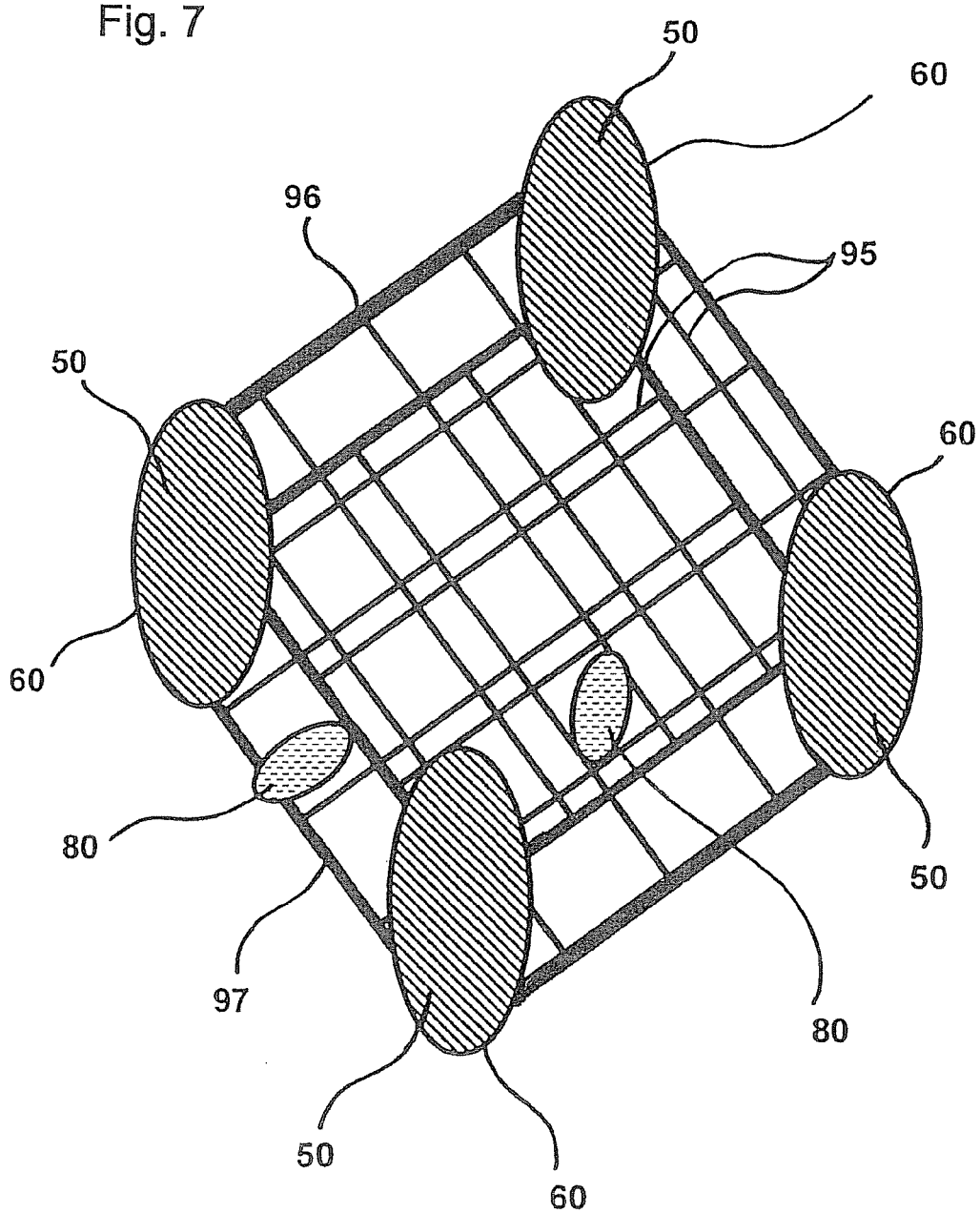

FIG. 7 schematically shows one preferred embodiment of four devices according to the invention which are connected to one another via a gridded framework.

DETAILED DESCRIPTION

FIG. 1 shows a kit 100 which contains an applicator syringe 10 made of sterilizable metal, on the open end 20 of which a disposable capsule 30, made of plastic, for example, is attached. The outwardly facing side of the disposable capsule 30 is provided with a protective cap 40. The disposable capsule 30 contains a plurality of devices 50 in the form of a granulate. The devices are injected via the syringe into a bone defect (not illustrated), for example in the jaw region.

The kit 100 according to the invention is used to inject the granulate composed of the devices 50 into a bone defect. After introduction into the bone defect, as a result of the structure and composition of the device according to the invention the volume of the swelling material 50 of the device changes, resulting in expansion, contraction, and/or change in shape of the sheathing of the device. The bone cells which in the meantime have become attached to the device are thus distracted for regeneration of the bone.

FIG. 2A shows a device 50, made of an elastic polymer, in a bone defect 200, specifically, immediately after this device 50 has been introduced into the bone defect 200, for example by use of a kit 100. The device 50 is composed of sheathing 60 and a swelling agent 70. After being introduced into the defect 200, the swelling agent 70 comes into contact with the liquid, in particular blood, present in the bone defect, thus causing the volume of the swelling agent 70 to become enlarged in the longitudinal axis, as schematically illustrated by the double arrow in FIG. 2A. This increase in volume of the swelling agent is accompanied by an expansion of the sheathing 60 in the longitudinal axis, resulting in an expanded sheathing 60 as shown in FIG. 2B. The expansion results in distraction of the cells 80 which have attached and adhered to the device 50.

FIG. 3 shows one preferred embodiment of the device 50, not to scale. This device is composed of tubular sheathing 60 which is designed partially as a corrugated hose or bellows 65 having folds 63. The tubular sheathing is closed at the tube ends. Not illustrated are pores in the sheathing 60, via which a liquid is able to pass through the sheathing 60 and to the swelling agent 70 present in the sheathing 60. As a result of the liquid absorption the swelling agent 70 is able to increase in volume, thus pushing apart the folds 63 of the part 65 of the sheathing 60 in the shape of a bellows or corrugated hose. This causes the sheathing 60 to expand along the length of the tube.

FIG. 4 shows another preferred embodiment of the device 50, not to scale. The basic structure corresponds to the embodiment shown in FIG. 3. The device 50 in FIG. 4 also has multiple lamellae 90 on the sheathing 60. The lamellae 90 are pushed apart as a result of the expansion of the sheathing 60 described in FIG. 3. Cells 80 which adhere to the lamellae experience biomechanical pulses as the result of distraction. The rod-like lamellae 90 illustrated in the longitudinal section may be layer- or leaf-shaped lamellae as viewed in three dimensions, which are situated around the entire circumference of the tubular sheathing 60 (compare to FIG. 5).

FIG. 5 shows a further preferred embodiment of the device 50, not to scale. This device has basically the same design, comprising sheathing having pores, and a swelling agent, as the device from FIG. 4. FIG. 5A shows this embodiment in the initial state. In this state the folds 63 of the corrugated hose 65 of the device 50 are folded together. The two planar lamellae 90 are thus separated by a distance, so that cells 80, for example osteoblasts, are able to bind to two lamellae 90. Of course, a device according to the invention may also have a plurality of lamellae 90. FIG. 5B shows the device 50 during or after the use according to the invention. Use of the device 50 causes the folds 63 of the corrugated hose 65 to be pushed apart due to the swelling agent 70, so that the two planar lamellae 90 are situated a farther distance apart. Adhering cells 80 thus experience an expansion pulse which allows distraction osteogenesis.

FIG. 6 shows a further preferred embodiment of the invention, not to scale. Two devices 50 are connected to one another via multiple lamellae 90. Of course, more than two devices 50 may be connected to one another via lamellae 90. The basic design of a device 50 corresponds to the embodiment shown in FIG. 4. As a result of the expansion, described in FIG. 3, of the sheathings 60 of the two devices 50, the lamellae 90 are pushed apart. Cells 80 which adhere to the lamellae experience biomechanical pulses as the result of distraction. The rod-like lamellae 90 illustrated in the longitudinal section may be layer- or leaf-shaped lamellae as viewed in three dimensions, which are situated around the entire circumference of the tubular sheathing 60.

FIG. 7 shows a further preferred embodiment of the invention, not to scale. Four devices 50 are connected to one another via a gridded framework 95. Of course, more than four devices 50 may be connected to one another via the framework 95. The devices 50 are composed of a capsule-shaped, expandable sheathing 60. The capsule-shaped sheathing encloses a swelling agent, not illustrated. Also not illustrated are pores in the sheathing 60, via which a liquid is able to pass through the sheathing 60 and to the swelling agent present in the sheathing 60. As a result of the liquid absorption the swelling agent is able to increase in volume, thus expanding the sheathings 60. This expansion of the sheathings 60 causes motion of the gridded framework 95. In particular, as a result of the expansion of the sheathings 60 the two grids 96 and 97 of the framework 95 are pushed apart. Cells 80 which adhere to the grids 96 and 97 experience biomechanical pulses as the result of distraction. Of course, the devices 50 may also be designed as shown in FIG. 3, i.e., with a tubular shape and having bellows.

The invention claimed is:

1. A granulate for regenerating a bone, the granulate comprising:
    a first device; and
    a second device;
    the first and second devices both including:
        a sheathing, at least a portion of the sheathing having a predefined shape in the form of a bellows; and
        a swelling agent completely enclosed by the sheathing for changing the shape of the sheathing in a predefined and controlled manner as a function of a force effect induced by a change in volume of the swelling agent the swelling agent cooperating with the sheathing such that a starting volume of the swelling agent changes at a predetermined rate and that a maximum rate at which the starting volume of the swelling agent is able to change is sufficient to distract cells adhering to the device a maximum of 1.5 mm per day;
    wherein the first and second devices cooperate to define the granulate.

2. The granulate according to claim 1, wherein a change in volume of the swelling agent is induced by the swelling agent as a result of absorption of liquid.

3. The granulate according to claim 1, wherein the swelling agent is a hydrogel.

4. The granulate according to claim 1, wherein the each sheathing contains a material selected from a group consisting of: polyglycolic acid, polylactic acid, poly($\epsilon$-caprolactone), poly($\beta$-hydroxybutyrate), poly(p-dioxanone), a polyanhydride, and mixtures thereof.

5. The granulate according to claim 1, wherein both of the sheathings are composed of polylactic acid.

6. The granulate according to claim 1, wherein the sheathings of both the first and second devices are composed of poly(ε-caprolactone).

7. The granulate according to claim 1, wherein the sheathings of both the first and second devices are biodegradable.

8. The device according to claim 1, wherein the sheathings of both the first and second devices are porous.

9. The device according to claim 1, wherein at least a portion of each sheathing has the shape of a tube.

10. The granulate according to claim 1, wherein the exterior of each sheathing bears at least one framework.

11. The granulate according to claim 1, wherein the first and second devices are connected to one another via at least one lamella.

12. The granulate according to claim 1, wherein the first and second devices are connected to one another via at least one framework.

13. The granulate according to claim 1, wherein the change in volume of the swelling agent is induced by the swelling agent as a result of absorption of liquid containing biomolecules or cells.

14. The granulate according to claim 1, wherein the change in volume of the swelling agent is induced by the swelling agent as a result of absorption of blood.

15. The granulate according to claim 1, wherein an exterior of the sheathings of the first and second devices are connected by at least two lamella, each sheathing having the shape of a bellows.

16. The granulate for regenerating a bone of claim 1, wherein the first and second devices are fixed to one another with a biodegradable adhesive.

17. The granulate for regenerating a bone of claim 1, wherein the granulate is injectable into a bone defect with a syringe.

18. A method for regenerating a bone, the method comprising:
providing a granulate including:
a first device; and
a second device;
the first and second devices both including:
a sheathing, at least a portion of the sheathing having a predefined shape in the form of a bellows; and
a swelling agent completely enclosed by the sheathing for changing the shape of the sheathing in a predefined and controlled manner as a function of a force effect induced by a change in volume of the swelling agent the swelling agent cooperating with the sheathing such that a starting volume of the swelling agent changes at a predetermined rate and that a maximum rate at which the starting volume of the swelling agent is able to change is sufficient to distract cells adhering to the device a maximum of 1.5 mm per day;
wherein the first and second devices cooperate to define the granulate;
introducing the granulate into a defect region of a bone; and
exposing the sheathing to a force effect as the result of the change in volume of the swelling agent.

19. The method according to claim 18, wherein the step of introducing the granulate into a defect region of a bone includes contacting the swelling agent with a liquid.

20. The method according to claim 18, further comprising revivifying the defect region of the bone before the granulate is introduced.

21. A granulate for regenerating a bone comprising:
first and second devices each including a sheathing;
a swelling agent enclosed by each of the sheathings, the swelling agent cooperating with a sheathing for changing a shape of the sheathing in a predefined and controlled manner as a function of a force effect induced by a change in volume of the swelling agent; and
at least two rigid lamellae extending distally between the sheathings of the first and second devices to generate a gridded framework;
wherein the sheathing and the swelling agent of both the first and second devices cooperate such that a starting volume of the swelling agent changes at a predetermined rate and that a maximum rate at which the starting volume of the swelling agent is able to change is sufficient to distract cells adhering to the device a maximum of 1.5 mm per day.

22. The granulate of claim 21, wherein the at least two lamellae includes at least one rod-shaped lamella.

23. The granulate of claim 21, wherein at least a portion of the sheathings of both the first and second devices has a predefined shape in the form of a bellows having a plurality of folds and wherein each rod-shaped lamella extends from a fold of the sheathing.

24. The granulate of claim 21, wherein the sheathing of both the first and second devices includes a first end and a second end and is elongated along an axis, and further wherein the at least two lamellae includes at least a pair of lamella spaced apart from both the first and second ends along a length of the sheathing.

25. The granulate for regenerating a bone of claim 21, wherein the granulate is injectable into a bone defect with a syringe.

26. A granulate for regenerating a bone, the granulate comprising:
a first device; and
a second device;
the first and second devices both including:
a porous sheathing comprising pores having a maximum size of 2 μm, at least a portion of the sheathing having a predefined shape in the form of a bellows;
a swelling agent completely enclosed by the sheathing for changing the shape of the sheathing in a predefined and controlled manner as a function of a force effect induced by a change in volume of the swelling agent the swelling agent cooperating with the sheathing such that a starting volume of the swelling agent changes at a predetermined rate and that a maximum rate at which the starting volume of the swelling agent is able to change is sufficient to distract cells adhering to the device a maximum of 1.5 mm per day; and
at least two rigid lamellae extending distally between the sheathings of the first and second devices to generate a gridded framework to define the granulate,
wherein the first and second devices are configured to allow liquid to penetrate the sheathing through the pores and contact the swelling agent to cause the swelling agent to expand.

* * * * *